United States Patent [19]
Harris

[11] Patent Number: 5,688,485
[45] Date of Patent: Nov. 18, 1997

[54] RADIOLABELLED COMPLEXES OF ESTER-SUBSTITUTED DIAMINETHIOLS

[75] Inventor: Thomas David Harris, Salem, N.H.

[73] Assignee: The DuPont Merck Pharmaceutical Company, Wilmington, Del.

[21] Appl. No.: 999,705

[22] Filed: Dec. 31, 1992

[51] Int. Cl.$^6$ .......................... A61K 51/04; C07F 13/00; C07C 321/00
[52] U.S. Cl. ..................... 424/165; 534/14; 560/147
[58] Field of Search ........................ 424/1.1, 1.65; 534/10, 14; 560/147

[56] References Cited

U.S. PATENT DOCUMENTS

| | | | |
|---|---|---|---|
| 4,444,690 | 4/1984 | Fritzberg | 534/14 X |
| 4,670,545 | 6/1987 | Fritzberg et al. | 534/14 |
| 4,673,562 | 6/1987 | Davison et al. | 424/1.1 |
| 4,849,511 | 7/1989 | Verbruggen | 424/1.1 X |
| 4,883,862 | 11/1989 | Chervu et al. | 424/1.1 X |
| 4,925,650 | 5/1990 | Nosco et al. | 424/1.1 |
| 4,965,392 | 10/1990 | Fritzberg et al. | 424/1.1 X |
| 4,980,147 | 12/1990 | Fritzberg et al. | 424/1.1 |
| 5,037,631 | 8/1991 | Nosco | 424/1.1 |
| 5,116,598 | 5/1992 | Nosco | 424/1.1 |
| 5,250,666 | 10/1993 | Gustavson et al. | 424/1.1 X |

FOREIGN PATENT DOCUMENTS

| 0279417 | 5/1992 | European Pat. Off. | A61K 43/00 |
|---|---|---|---|

OTHER PUBLICATIONS

*Concise Encyclopedia Chemistry*, 1994, p. 925.

*Primary Examiner*—John Kight
*Assistant Examiner*—Lara C. Kelley
*Attorney, Agent, or Firm*—Gerald J. Boudreaux; David H. Vance

[57] ABSTRACT

This invention relates to compounds and methods for use in determining renal function by means of scintigraphic urography. More specifically, this invention relates to radionuclide complexes of ester-substituted diaminethiols, radiopharmaceutical compositions comprising said complexes, kits for the preparation of said compositions, and a method of using said compositions for examining renal function. Compounds of this invention have the formula:

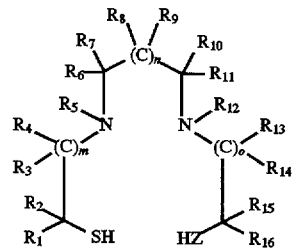

wherein the various groups are as defined herein.

4 Claims, No Drawings

RADIOLABELLED COMPLEXES OF ESTER-SUBSTITUTED DIAMINETHIOLS

FIELD OF THE INVENTION

This invention relates to compounds and methods for use in determining renal function by means of scintigraphic urography. More specifically, this invention relates to radionuclide complexes of ester-substituted diaminethiols, radiopharmaceutical compositions comprising said complexes, kits for the preparation of said compositions, and a method of using said compositions for examining renal function.

BACKGROUND OF THE INVENTION

Radiopharmaceutical compounds have been in use for diagnostic purposes for many years and are capable of detecting deviations in the shape and function of internal organs, and also the presence and location of pathological processes in the body. One skilled in the art of nuclear medicine and radiopharmaceutical research is well aware of the requirements for a diagnostically useful radiopharmaceutical. Briefly, these requirements include: efficient preparation of the radiopharmaceutical, such that preparation in the hospital or pharmacy is possible; administration to the patient, such as by injection; efficient transport of the radiopharmaceutical to the target organ; efficient extraction of the radio-pharmaceutical by the target organ, such that adequate target to background ratios are achieved to allow diagnostic distinctions; adequate retention in the target organ to allow detection using conventionally available radiation monitoring equipment.

The kidneys are the body organs primarily responsible for regulation of the composition of body fluids. The kidneys clear the blood of unwanted metabolic end products (such as urea and uric acid) and excess nonmetabolic substances (such as water, sodium and potassium). The functioning of the kidneys is determined by a combination of glomerular filtration and tubular secretion. In glomerular filtration a portion of the plasma passively diffuses across the glomerular membrane. In addition to this passive diffusion, some ionic compounds are actively secreted into the tubules of the kidneys. For example, p-aminohippuric acid (PAH) is approximately 70% removed from the plasma by active secretion into the tubules.

A number of renal function tests are available to the physician to evaluate the extent and type of kidney dysfunction. One such procedure is known as scintigraphic urography (also known as a dynamic renal function imaging study). This procedure involves the intravenous administration of a radioactively labelled substance. The rate at which this radioactive substance is eliminated by the kidneys is followed by the use of a gamma scintillation camera, thereby giving an indication of the quality of renal function. Compounds which have been used for examining kidney function include radioactive I-131-o-iodohippurate (I-131-OIH), Tc-99m-diethylenetriamine pentaacetic acid (Tc-99m-DTPA), and Tc-99m-mercaptoacetyltriglycine (Tc-99m-MAG3).

Like PAH, I-131-OIH is rapidly removed from the blood by active tubular secretion, and has been an important tool in evaluating renal function. However, it suffers from some significant drawbacks. First, I-131 emits a high energy gamma particle (364 KeV) which results in images having poor resolution. Second, I-131-OIH constitutes a significant radiation burden to the patient because it emits a beta particle which is injurious to surrounding tissue, and because the free I-131 which accompanies I-131-OIH is readily taken up by the thyroid gland. This limits the dose of I-131-OIH to only 200–300 microcuries, as a result of which the resulting signal is insufficient to obtain statistically reliable images of kidney function by means of a gamma camera. Finally, the renal extraction efficiency of I-131-OIH is about 65–80%. This is considered good, but a higher extraction fraction would allow better measurement of minimal renal function. Another radioactive OIH compound frequently used for examining kidney function is I-123-OIH, which offers a much lower radiation burden to the patient. I-123 compounds, however, have a restricted availability due to the short half-life of 13.3 hours, and because the production of I-123 must be carried out in a cyclotron.

Tc-99m is considered one of the best radionuclides for performing imaging studies. It emits a 140 KeV gamma particle, making it compatible with modern gamma cameras. It has a half-life of about 6 hr, which results in a low radiation dose per millicurie. Doses as high as 30 millicuries of Tc-99m can be safely administered to a patient. The high dosage possible and the energy of the gamma particle result in short imaging times and superior image quality. Tc-99m can be prepared at the work site by the use of a portable generator.

Tc-99m-DTPA has good image characteristics because of the Tc-99m radionuclide, but it appears to be eliminated entirely or nearly entirely by glomerular filtration. This means it has a maximum extraction efficiency of only 20–25%, making it less useful in detecting mild renal dysfunction.

Another Tc-99m complex reported to be useful in evaluating renal function is Tc-99m-N,N'-bis(mercaptoacetyl) ethylenediamine (Tc-99m-DADS). This complex is excreted by active tubular secretion, but has an extraction efficiency of only about 53%.

European Patent Application 73424 discloses the preparation of the complex Tc-99m-MAG3, which is secreted by the kidneys selectively by tubular secretion and approximately as rapidly as OIH. However, the organ specificity of this complex is less than desired. Chemically related compounds having an improved organ specificity are the subject of European Patent 250013. The shelf life of the Tc-99m complexes described in these European patent applications is only a few hours. This is less than ideal because it is often desirable to have an imaging agent available for immediate use, for example in an emergency room. Furthermore the conditions required to prepare the labelled product from the kit are less than ideal. In order to prepare the Tc-99m complexes described in these European patent applications, the kit contents must be heated in a boiling water bath for five minutes with eluate from a technetium generator. This is inconvenient and carries with it the possibility of accidental release of radioactivity due to broken vials.

Clearly the need exists for more effective and convenient radiopharmaceuticals for the evaluation of kidney function. It would be a substantial improvement in the field of renal imaging to have a Tc-99m complex which had a high extraction efficiency, could be conveniently and safely prepared, and had a long shelf-life.

European Patent 0279417 discloses the preparation and use of radiolabelled complexes of ester-substituted diaminedithiols for the evaluation of regional cerebral blood flow. The Tc-99m complexes of these diaminedithiols are neutral, lipophilic complexes, which are readily taken up by the primate brain. Once in the brain, an esterase hydrolyzes one of the ester groups to yield a polar metabolite which will not pass through the blood brain barrier, thus providing long-term image stability.

U.S. Pat. No. 4,925,650 discloses the use of the chemically related carboxyl-substituted diaminedithiols as renal imaging agents.

It is an object of the present invention to provide radiolabelled complexes suitable for examining the kidney function. Said complexes will show high organ specificity, high image quality, and long stability. It is also an object of the present invention to provide kits for the preparation of said complexes. Such kits will allow for a convenient and safe preparation of said complexes.

DETAILED DESCRIPTION OF THE INVENTION

To achieve these objectives there is provided an ester-substituted diaminethiol of the general formula:

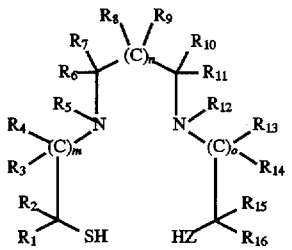

I or a pharmaceutically suitable salt thereof wherein:

$R_1$–$R_{18}$ are independently selected from the group consisting of:

H, straight or branched, substituted or unsubstituted alkyl of 1–5 carbon atoms, and —A—COOR, wherein A is a straight or branched, substituted or unsubstituted alkyl group having 0–5 carbon atoms and R is:

(a) alkyl of 1–5 carbon atoms, (b) phenyl or benzyl optionally substituted with up to 5 ring substituents each selected from alkyl of 1–5 carbon atoms, fluoro, chloro, bromo, nitro, alkoxy of 1–5 carbon atoms, carboxyl, or a carboxylic acid ester of 1–5 carbon atoms, or (c) a 5- or 6-membered heterocyclic ring containing 1 or 2 heteroatoms selected from N, O, or S;

additionally, $R_6$ together with $R_7$, or $R_{10}$ together with $R_{11}$, or $R_3$ together with $R_4$, or $R_{13}$ together with $R_{14}$ independently may form an oxygen atom;

Z is S, O, or an amino group of the general formula $R_{17}$—N—$R_{18}$;

m and o are independently either 1 or 2; and n is 0 or 1;

provided that:

(a) at least one of $R_1$–$R_{18}$ is —A—COOR, and (b) at least one of the following form an oxygen atom:
$R_6$ together with $R_7$, or
$R_{10}$ together with $R_{11}$, or
$R_3$ together with $R_4$, or
$R_{13}$ together with $R_{14}$.

Pharmaceutically suitable salts may be salts of mineral acids such hydrochloric acid, sulfuric acid, phosphoric acid, perchloric acid, or organic acids such as citric acid, oxalic acid, tartaric acid, and the like.

Further provided is a radiopharmaceutical consisting of a complex of an ester-substituted diaminethiol as described above and a radionuclide, having the general formula:

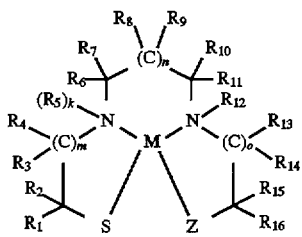

II wherein:

M is a radionuclide selected from the radioactive isotopes of Tc, Ru, Cu, Co, Pt, Fe, Os, Ir, W, Re, Cr, Mo, Fin, Ni, Rh, Pd, Nb, and Ta; m is 0 or 1;

$R_1$–$R_{18}$ are independently selected from the group consisting of:

H, straight or branched, substituted or unsubstituted alkyl of 1–5 carbon atoms, and —A—COOR, wherein A is a straight or branched, substituted or unsubstituted alkyl group having 0–5 carbon atoms and R is:

(a) alkyl of 1–5 carbon atoms, (b) phenyl or benzyl optionally substituted with up to 5 ring substituents each selected from alkyl of 1–5 carbon atoms, fluoro, chloro, bromo, nitro, alkoxy of 1–5 carbon atoms, carboxyl, or a carboxylic acid ester of 1–5 carbon atoms, or (c) a 5- or 6-membered heterocyclic ring containing 1 or 2 heteroatoms selected from N, O, or S;

$R_6$ together with $R_7$ or $R_{10}$ together with $R_{11}$ additionally may form an oxygen atom;

$R_3$ together with $R_4$ or $R_{13}$ together with $R_{14}$ additionally may form an oxygen atom;

Z is S, O, or an amino group of the general formula $R_{17}$—N—$(R_{18})_p$;

m and o are independently 1 or 2; and k, n and p are independently 0 or 1;

with the proviso that at least one of $R_1$–$R_{18}$ is —A—COOR.

When the symbols k and/or p are/is 1, there is a coordinative bond between the amino nitrogen and M. The above general formula also includes the stereoisomeric structures in which N-$(R_5)_k$ has been exchanged with N-$R_{12}$, or S has been exchanged with Z.

Also provided is a kit which comprises a predetermined quantity of a sterile, pharmaceutically acceptable ester-substituted diaminethiol as described above and a predetermined quantity of a sterile, non-pyrogenic reducing agent for reducing a preselected radionuclide. Such kit may also contain non-reactive components such as buffer and filler.

Additionally provided is a process of radioimaging comprising administering parenterally a radiopharmaceutical as set forth above in a pharmaceutically suitable carrier and radioimaging the kidneys using conventionally available radiation monitoring equipment.

Preferred Embodiments

It is preferred that the compound of formula I be a diaminedithiol. For the purposes of this invention, a "diaminedithiol" will be understood to be an organic ligand, which utilizes two amines and two thiols to coordinate with a radioactive metal, which may be unsubstituted or substituted on any or all of the carbon atoms.

Preferred diaminedithiols include, but are not limited to, 1,10-dithia-4,7-diazadecanes, 1,12-dithia-5,8-diazadodecanes, 1,11-dithia-4,7-diazaundecanes, 1,11- dithia-4,8-diazaundecanes, 1,11-dithia-4,8-diazaundecane-5,7-diones, and 1,10-dithia-4,7-diazadecane-3,8-diones.

It is preferred that the diaminedithiol be non-aminated and non-thiolated. "Non-aminated" and "non-thiolated" will be understood to mean that there are no additional amine substituents or thiol substituents on any of the carbon atoms of the diaminedithiol.

Because of its ready availability and radiological properties the preferred radionuclide is technetium-99m.

These preferred embodiments can be represented by general formula III:

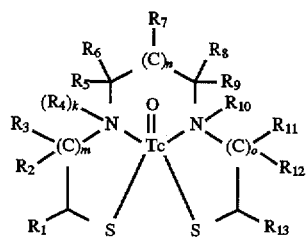

III

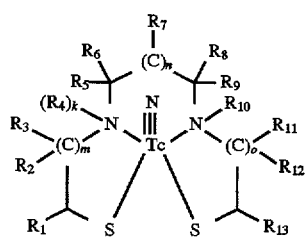

IV wherein:

$R_1$–$R_{13}$ are independently selected from the group:
H, straight or branched, substituted or unsubstituted alkyl of 1–3 carbon atoms, and —A—COOR, wherein A is a straight or branched, substituted or unsubstituted alkyl of 0–3 carbon atoms and R is alkyl of 1–3 carbon atoms;

additionally, $R_2$ together with $R_3$, or $R_5$ together with $R_6$, or $R_8$ together with $R_9$, or $R_{11}$ together with $R_{12}$ independently may form an oxygen atom;

m and o are independently either 1 or 2; n is 0 or 1;

with the proviso that 1–4 of $R_1$–$R_{13}$ must be —A—COOR.

When the radionuclide is technetium-99m in the form of the Tc<sup>v</sup>O core, one of the amines of the diaminedithiol is deprotonated in the radiopharmaceutical complex to result in a complex which is charge neutral. In this case k is 0. In addition to the Tc<sup>v</sup>O core, complexes can be formed which incorporate the TcN core, and in which both amines of the diaminedithiol complex remain protonated. This is represented by general formula IV. The above general formula also includes the stereoisomeric structures in which N-($R_4$)$_k$ has been exchanged with N-$R_{10}$.

Particularly preferred radiopharmaceuticals are prepared from diaminedithiols according to general structures III and IV wherein:

$R_1$–$R_{13}$ is independently selected from the group:
H, straight chain alkyl of 1–3 carbon atoms, and —A—COOR, wherein A is a bond and R is alkyl of 1–3 carbon atoms; and m and o are 1; n is 0;

provided that 1–4 of $R_1$–$R_{13}$ is —A—COOR.

Specifically preferred radiopharmaceuticals are the technetium-99m complexes of (1) (D,L)-N,N'-1,2-ethylenediylbiscysteine, diethyl ester; (2) (D,L)-N,N'-1,2-ethylenediylbiscysteine, dimethyl ester; and (3) (D,L)-N,N'-1,2-ethylenediylbiscysteine, di-n-propyl ester.

SYNTHESIS

The diaminedithiol ligands of the present invention can be prepared by several methods of coupling appropriately substituted (and in some cases protected) amine, thiol, and aminethiol fragments. Preparation of the necessary fragments is possible by a wide variety of techniques known to one skilled in the art of organic synthesis. In the following reaction descriptions, $R_1$–$R_{14}$ are as described above except where stated to the contrary.

The specifically preferred ligands can be prepared by the diaminedithiol forming reactions which include the reductive dimerization of substituted thiazolidines or a tetrahydro-1,3-thiazene of formula V to give the diaminedithiol acids of formula These can be esterified by reaction with an appropriate alcohol and catalyst to afford the ester-substituted diaminedithiols of formula VII (Scheme I). This general synthesis of ester-substituted diaminedithiols has been described by Blondeau el al., Can. J. Chem. 1967, 45, 49, and in European Patent which are incorporated herein by reference.

Scheme I

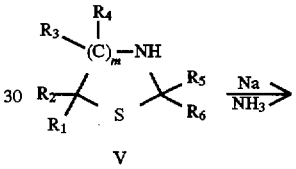

V

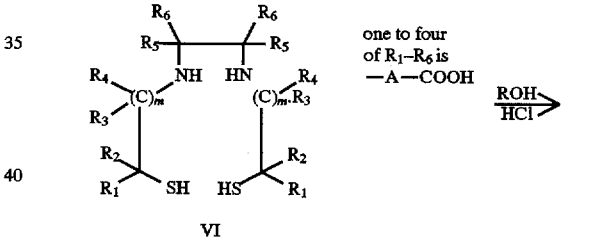

VI

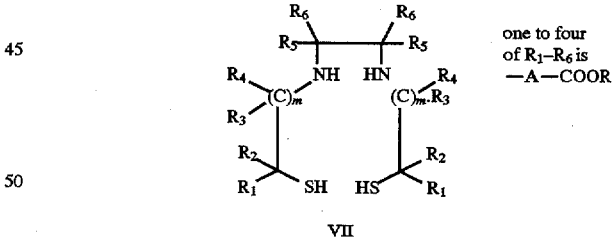

VII

In particular, a thiazolidine or a tetrahydro-1,3-thiazene of formula V can be reacted with sodium in liquid ammonia, followed by esterification with an alcohol such as methanol or ethanol using gaseous hydrogen chloride as catalyst to afford a compound of formula VII. Thiazolidines and tetrahydro-1,3-thiazenes of formula V are prepared by reaction of an amine-thiol with an aldehyde or ketone as described by M. T. Nagasawa et al., J. Med. Chem. 1984, 27, 591, which is incorporated herein by reference.

Alternatively, a diaminedithiol can be prepared by the reductive amination of gloxal or a 1,2-diketone or 1,3-diketone moiety of formula VIII with an appropriately substituted (and protected) aminethiol of formula IX (Scheme II).

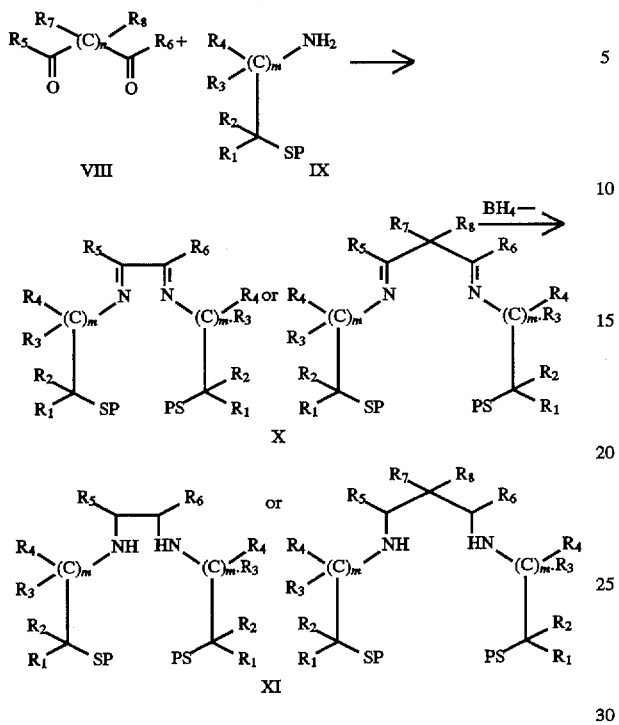

Scheme II

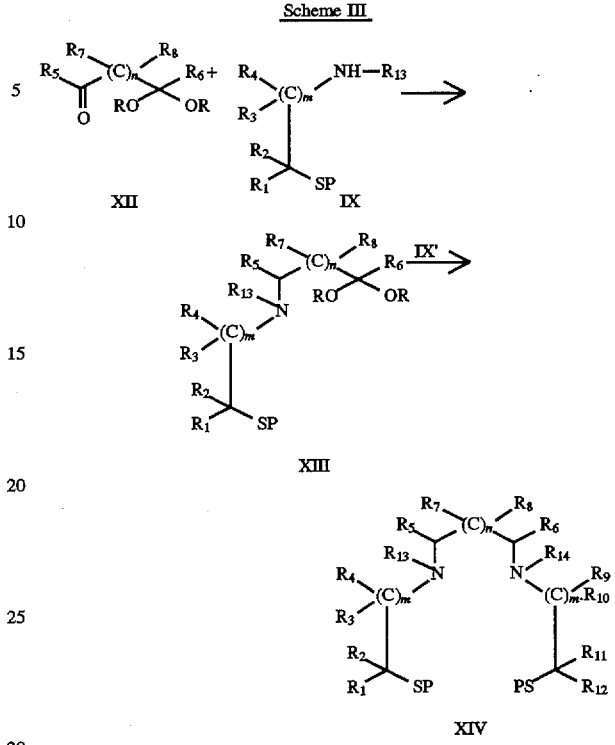

Scheme III

In particular, reaction of glyoxal or a ketone moiety with a protected aminethiol moiety in the presence of a dehydrating agent such as a molecular sieve, followed by reduction of the diimine intermediate (formula X) with a borohydride reducing agent affords a protected diaminedithiol of formula XI. Protecting group P can be any of a variety of protecting groups for sulfur, and includes trifluoroacetyl, methoxymethyl, methoxyethoxymethyl, p-methoxybenzyl, or benzyl. These protecting groups can be added and removed by appropriate methods well known to one skilled in the art of organic synthesis, and include trifluoroacetic acid, sodium in liquid ammonia, or mercuric chloride. See, for example, T. W. Greene, *Protective Groups in Organic Synthesis*, (John Wiley & Sons). With Lewis acid labile protecting groups such as acetamidomethyl and benzamidomethyl, the protecting group can be left intact. In these cases labelling of the ligand with technetium will cleave the group P thus rendering the protected diaminedithiol equivalent to the unprotected form.

For the preparation of unsymmetrical diaminedithiol ligands, a protected form of a compound of formula VIII, such as XII, can be used in a stepwise coupling sequence as shown in Scheme III. A protected aminethiol of formula IX is reductively aminated with a compound of formula XII to afford protected carbonyl compound of formula XIII. Deprotection, followed by reductive amination with a second aminethiol (IX') affords the unsymmetrical diaminedithiol ligand of formula XIV, which may be deprotected by an appropriate method, as described above. The reaction conditions are essentially the same as for the reactions of Scheme II.

Diamidodithiol ligands of formula XVII can be prepared by coupling a 1,2-diamine or 1,3-diamine moiety of formula XV with an appropriately substituted and protected thioglycolic acid derivative of formula XVI as shown in Scheme IV. See E. Deutsch et al., *J. Med. Chem.* 1992, 35, 274–279, which is incorporated herein by reference. Protecting group P can be any of a variety of protecting groups for sulfur as described above for Scheme II. Leaving group L can be any group which increases the reactivity of carboxyl groups toward substitution, and includes alkyl and aryl esters, N-hydroxysuccinimide esters, halides, and mixed anhydrides. For cases where L is a less reactive leaving group, such as simple alkyl or aryl esters, no protection on sulfur may not be needed (P=H). In practice this route yields diamidodithiol ligands in essentially a single step.

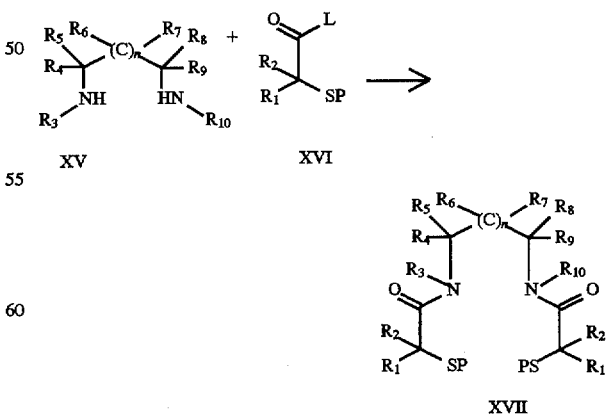

Scheme IV

The structurally similar diamidodithiol ligands of structure XIX can generally be prepared by coupling appropriately substituted (and in some cases protected) aminethiols of formula IX with an appropriately substituted 1,2-dicarboxylic acid or 1,3-dicarboxylic moiety of structure XVIII (Scheme V). Protecting group P can be any of a variety of lo protecting groups for sulfur as described above for Scheme II. Leaving group L can be any group which increases the reactivity of carboxyl groups toward substitution, as described above.

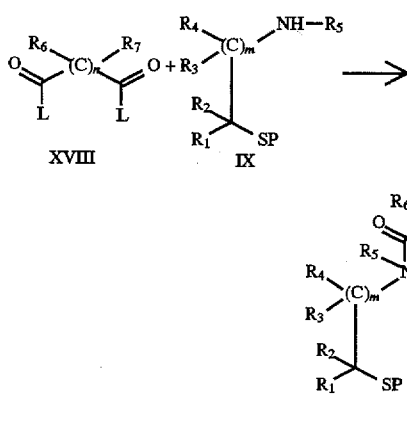

Scheme V

The radiopharmaceutical complexes of the present invention can easily be prepared by admixing a salt of a radioactive metal and the ligand in the presence of a suitable reducing agent, if required, in aqueous media at temperatures ranging from ambient temperatures to reflux temperature or even higher, and are obtained and isolable in high yield at both macro (carrier added, e.g., Tc-99) concentrations and at tracer (no carrier added, e.g., Tc-99m) concentrations of less than $10^{-6}$ molar. Suitable additional reducing agents are well known to those skilled in the art, and include dithionite, formamidine sulphinic acid, diaminomethane disulphinate, sodium borohydride, or suitable metallic reducing agents such as Sn(II), Fe(II), Cu(I), Ti(III), or Sb(III). Sn(II) has proven to be particuarly suitable. In some cases the diaminethiol ligand may itself act as the reducing agent, thus eliminating the need for an additional reducing agent. The reaction is generally complete after one minute to two hours, depending upon the identity of the particular reagents employed.

In the case of technetium such as, for example Tc-99 or Tc-99m, a complex in accord with this invention is preferably made by mixing pertechnetate ($TcO_4^-$) with the desired diaminethiol in aqueous medium, then adding to the reaction mixture an appropriate reducing agent capable of reducing the technetium. The preferred reducing agent is a stannous salt such as stannous chloride or stannous glucoheptonate. It has been found that the specifically preferred radiopharmaceuticals are formed at ambient temperatures in radiochemical yields exceeding 90%. Thus, heating of the reaction mixture is not necessary for conversion to the desired Tc-99m complex.

Alternatively, the Tc-99m complexes of this invention can also be prepared in ligand exchange reactions from preformed complexes of technetium with relatively weak chelators. Examples of suitable chelators are dicarboxylic acids, polycarboxylic acids, or hydroxy carboxylic acids, such as oxalic acid, malonic acid, succinic acid, maleic acid, o-phthalic acid, lactic acid, tartaric acid, citric acid, ascorbic acid, salicylic acid, or derivatives of these acids; phosphorus compounds such as pyrophosphates; or enolates. Citric acid, tartaric acid, ascorbic acid, glucoheptonic acid or a derivative thereof are particularly suitable chelators for this purpose, because it appears that a chelate of Tc-99m with one of these chelators undergoes the desired ligand exchange particularly easily.

An excess of the diaminethiol ligand, up to 50 to 100 fold molar excess or more, and an excess of reducing agent, can be used in the complexing reaction to ensure maximum yield of the radiopharmaceutical. Following the reaction, the desired complex can be separated from the reaction mixture, if required, by crystallization or precipitation or conventional chromatography.

This invention also relates to kits for the preparation of radiopharmaceuticals which comprise a sterile, non-pyrogenic diaminethiol ligand of general formula I, wherein the symbols have the meanings already discussed. The particularly preferred kit comprises a diaminedithiol ligand of general formula XX:

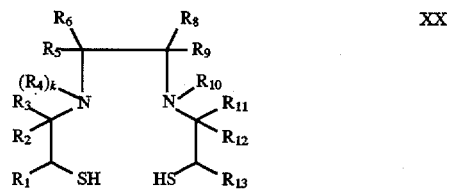

XX wherein:

each of $R_1$–$R_{13}$ is individually selected from H, straight chain alkyl of 1–3 carbon atoms, and —A—COOR, wherein A is a bond and R is alkyl of 1–3 carbon atoms; the proviso that at least one, but preferably no more than four, of $R_1$–$R_{13}$ is —A—COOR.

Additionally, the kit may contain a predetermined quantity of a sterile reducing agent, if necessary, capable of reducing a predetermined quantity of a preselected radionuclide. The kit may also contain a predetermined quantity of a sterile chelator, if necessary, and a pharmaceutically acceptable carrier. Examples of suitable reducing agents and chelators have already been discussed. The preferred reducing agent is a stannous salt such as stannous chloride or stannous glucoheptonate.

The contents of the above kit may be delivered as a solution, for example, in the form of a physiological saline solution, or in some buffer solution, but it is preferred that the kit be lyophilized to facilitate storage stability. If lyophilization is not practical, the kit may be stored frozen, or in solution at ambient temperatures. The choice of radionuclides will in general be dependent on the final use of the labelled product. Because of the availability of Tc-99m generators, such a radionuclide is especially preferred.

In one embodiment of the invention, a kit for use in making the complexes of the present invention from a supply of Tc-99m such as the pertechnetate solution in isotonic saline available in most clinical laboratories includes the desired quantity of a selected ligand to react with a selected quantity of pertechnetate, and a reducing agent such as stannous chloride in an amount sufficient to reduce the selected quantity of pertechnetate to form the desired complex.

The stereochemical configuration of the Tc-99m complex is determined in part by the configuration of the starting diaminethiol ligand of general formula I or XX above. Different stereoisomers of these ligands can be separated from each other by using techniques known to one skilled in the art, such as recrystallization, chromatographic techniques, and sublimation. A particularly suitable method of preparing stereochemically pure diaminethiol ligands consists in using starting materials which are already stereochemically pure, and ensuring that during the synthesis of the intended ligand no racemization occurs. With some ligands and with certain radionuclides the complex may form in more than one stereochemical form. As an example, consider the stereochemically pure diaminedithiol D,L-ligand of general formula XXI (Scheme VI). Complexation with technetium forms the Tc^VO core and the possibility of forming two stereoisomeric complexes; complex XXII, generally referred to as the syn form, and complex XXIII, generally referred to as the anti form. If desired, these different stereoisomers can be separated from each other by using techniques of separation known to one skilled in the art.

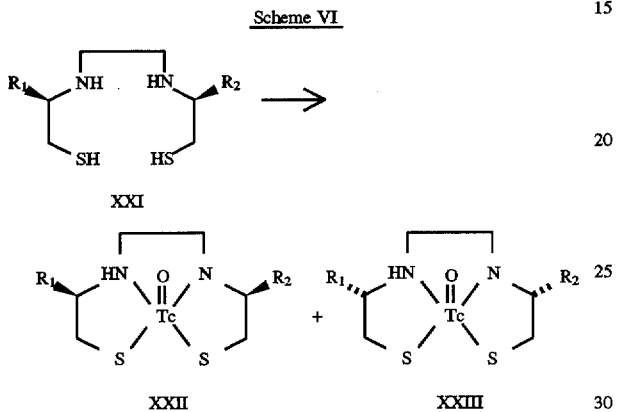

Scheme VI

A preferred kit for the facile preparation of the desired Tc-99m radiopharmaceutical, in accordance with the present invention, is comprised of two vials. One vial (A) contains the ester-substituted diaminedithiol ligand prepared in lyophilized form at acidic pH, where ligand stability is optimal, and an inert filler, such as mannitol, to provide easy lyophilization. The second vial (B) contains a reductant suitable to convert the Tc-99m to the desired oxidation state and an inert filler such as mannitol. The second vial is lyophilized at a pH of approximately 9. When the contents of the vials are mixed together with sterile saline, an optimal pH of 3.0–5.0 is obtained. This provides optimal reaction of the diaminedithiol ligand with the reduced Tc-99m to prepare the desired radiopharmaceutical in high yield and high purity. One method by which the Tc-99m radiopharmaceutical can be prepared in high yield is as follows:

One vial (A) is prepared as a sterile, non-pyrogenic, freeze-dried material containing the dihydrochloride salt of the ester-substituted diaminedithiol ligand at levels of 100 ug to 2 mg, or higher, with a suitable inert filler such as mannitol, to provide a suitable plug after freeze-drying.

The second vial (B) is prepared as a sterile, non-pyrogenic, freeze-dried material containing a suitable reductant, such as a stannous salt (e.g., $SnCl_2$) at levels of 5 ug to 100 ug, or more. Vial B may also contain a ligand to stabilize Sn(II), such as ethylene diamine tetraacetic acid (EDTA) at a level of 100 ug to 1.0 mg, or more. In addition, a bulking agent such as mannitol may be used to aid in lyophilization.

The Tc-99m radiopharmaceutical, as described in the present invention, is prepared by admixing the contents of vials A and B with Tc-99m $TcO_4^-$ from a Mo-99/Tc-99m radiopharmaceutical generator using sterile techniques well known to those skilled in the art of preparing sterile injectable materials. The generator eluant added should provide about 20–50 mCi of activity. After 15 minutes at ambient temperatures, the Tc-99m diaminedithiol complex, as described herein, is formed in high radiochemical yield (e.g., 80%).

EXAMPLES

The following examples illustrate the preparation of ester-substituted diaminedithiol ligands and Tc-99m complexes of the present invention. The following examples and preparations are for illustrative purposes only and are not to be construed as limiting the invention.

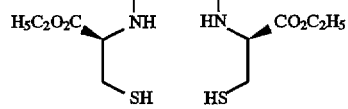

Example 1

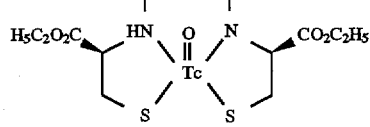

Example 2

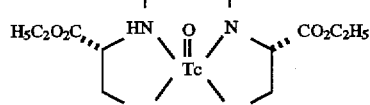

Example 3

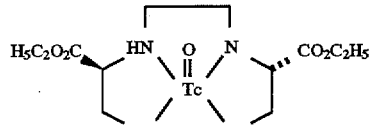

Example 4

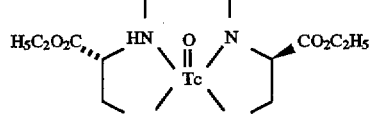

Example 5

These Tc-99m complexes were prepared using standard labelling conditions similar to those reported in the literature for other diaminedithiol ligands. Diaminedithiol ligands (L,L)-N,N'-1,2-ethylenediylbiscysteine, diethyl ester, and (D,D)-N,N'-1,2-ethylenediylbiscysteine, diethyl ester were prepared as the dihydrochloride salts by a published procedure (European Patent 0279417) beginning respectively with the sodium salts of L-thiazolidine-4-carboxylic acid and D-thiazolidine-4-carboxylic acid. (D,L)-N,N'-1,2-ethylenediylbiscysteine, diethyl ester, (Example 1) was separated from a racemic mixture of the ligand, as described below. The racemic ligand was also prepared according to European Patent 0279417 from racemic thiazolidine-4-carboxylic acid.

The separation of (D,L)-N,N'-1,2-ethylenediylbiscysteine, diethyl ester from the racemic mixture was carried out on the zinc complex of the ligand using a combination of HPLC and recrystallization. The zinc complex of the racemic mixture was prepared using zinc acetate. (D,L)-Zn-N,N'-1,2-ethylenediylbiscysteine, diethyl ester has a substantially longer retention time on a HPLC C8 support than either the L,L or D,D zinc complexes using either water/methanol or water/acetonitrile mobile phases. Such separation gave the D,L isomer in a stereochemical purity >98%. Stereochemical purity >99% was achieved by recrystallization from a minimal amount of hot acetonitrile.

The zinc atom was removed from the purified complex by treatment with oxalic acid.

Examples 2 (syn isomer) and 3 (anti isomer) were prepared simultaneously as a mixture of stereoisomers from the D,L ligand and were separated by HPLC chromatography. Examples 3 and 4 were prepared stereochemically pure from the L,L and D,D isomers respectively.

Example 1

Synthesis of (D,L)-N,N'-1,2-ethylenediylbiscysteine, diethyl ester, oxalate

A solution of zinc acetate dihydrate (9,10 g, 0.042 mol) and sodium acetate trihydrate (4.80 g, 0.035 mol) in water (200 mL) was added to a solution of racemic N,N'-1,2-ethylenediylbiscysteine, diethyl ester, dihydrochloride (10.0 g, 0.025 mol) and sodium acetate trihydrate (4.80 g, 0.035 mol) in water (200 mL). A milky white precipitate formed immediately. The mixture was stirred under nitrogen at ambient temperatures for 1.5 hr. The precipitate was extracted into methylene chloride (3×125 mL). The combined organic extracts were dried (MgSO$_4$) and concentrated to give 10.11 g of racemic Zn-N,N'-1,2-ethylenediylbiscysteine, diethyl ester as a yellow amorphous solid.

The crude product from above was dissolved in methanol (50 mL) and purified in 25 equal portions on a Waters C8 Bondapak® 4.7 cm×30 cm 15–20 micron HPLC column using a 40% aqueous methanol mobile phase at a flow rate of 60 mL/min. The L,L and D,D isomers co-eluted in a broad peak between 8 and 10 min, while the D,L isomer eluted in a very broad peak between 10 and 18 min. Concentration of the pooled product fractions gave 3.47 g of (D,L)-Zn-N,N'-1,2-ethylenediylbiscysteine, diethyl ester as a pale yellow solid. Analytical HPLC analysis of this solid on a Zorbax® RX-C8 4.6 mm×25 mm column using 30% aqueous acetonitrile as the mobile phase and a flow rate of 1 mL/min indicated a stereochemical purity of 98.27%. Further purification was achieved by recrystallization from the minimal amount of hot acetonitrile (425 mL) to give 2.14 g of colorless solid, MP (dec) 234°–239° C. HPLC analysis indicated a stereochemical purity of 99.64%. A second recrystallization from acetonitrile (275 mL) gave 1.96 g of (D,L)-Zn-N,N'-1,2-ethylenediylbiscysteine, diethyl ester as a colorless solid, MP (dec) 235°–239° C. with a stereochemical purity of 99.88%. IR, $^1$H NMR, and $^{13}$C NMR spectroscopy and mass spectrometry were consistent with this structure.

(D,L)-Zn-N,N'-1,2-ethylenediylbiscysteine, diethyl ester (1.74 g, 4.47 mol) was dissolved with heating in 50% aqueous acetonitrile (225 mL). The solution was cooled to near ambient temperatures and treated with 0.5M oxalic acid in 50% aqueous acetonitrile (22 mL, 11 mmol). A large amount of colorless solid precipitate formed. After cooling in an ice bath for 1 hr the precipitate was removed by filtration, washed with 50% aqueous acetonitrile, and dried to give 2.58 g of colorless solid. This solid was recrystallized from water (90 mL) to give 1.19 g of colorless solid. The mother liquor gave another 108 mg of colorless solid. These two crops were combined and recrystallized from water (60 mL) to give 682 mg of (D,L)-Zn-N,N'-1,2-ethylenediylbiscysteine, diethyl ester oxalate as a colorless solid, MP 172°–173° C. IR, $^1$H NMR, and $^{13}$C NMR spectroscopy and mass spectrometry were consistent with this structure. Elemental analysis was correct to within 0.4% on all elements present. The stereochemistry of the ligand was confirmed by preparation of the Re(O)ECD complex, separation of the syn and anti isomers, and determination of the crystal structure of the syn isomer.

Elemental Analysis of (D,L)-N,N'-1,2-ethylenediylbiscysteine, diethyl ester, oxalate:

| Element | Calculated | Found |
|---------|------------|-------|
| C | 40.57 | 40.33 |
| H | 6.32 | 6.27 |
| N | 6.76 | 6.65 |
| S | 15.47 | 15.49 |

Example 1A

Synthesis of syn-Re-(D,L)-N,N'-1,2-ethylenediylbiscysteine, diethyl ester

Racemic N,N'-1,2-ethylenediylbiscysteine, diethyl ester, dihydrochloride (2.00 g, 5.08 mmol), ammonium perrhenate (4.24 g, 15.8 mmol), and sodium bicarbonate (0.88 g, 14.8 mmol) were added with stirring to low oxygen water (600 mL) in a 1 L round bottom flask. The mixture was sonicated until all the solids dissolved (10 minutes). The solution was purged with nitrogen for 15 minutes and treated with a solution of sodium dithionite (6.80 g, 40.0 mmol) in low oxygen water (100 mL) dropwise over 5 minutes. The clear solution was tightly stoppered and allowed to react at ambient temperatures for 15 hrs. The reaction mixture now consisted of a pale yellow solution and a brown solid precipitate. The solid was extracted into chloroform (3×200 mL). The combined organic extracts were dried (MgSO$_4$) and concentrated to yield 2.46 g (93%) of crude complex.

Initial separation of syn-Re-(D,L)-N,N'-1,2-ethylenediylbiscysteine, diethyl ester was accomplished by HPLC chromatography on a Waters C8 Bondapak® 4.7 cm×30 cm 15–20 micron column using a linear gradient beginning with 10% aqueous acetonitrile increasing to 55% acetonitrile in 45 minutes, and a flow rate of 75 mL/min. The 2.46 g sample from above was dissolved in 10 mL of acetonitrile and purified in 10 equal portions. The chromatogram consisted of two broad peaks centered at 35 and 37 minutes. The 35 minute peak was composed of incompletely separated anti; L,L; and D,D isomers, while the 37 minute peak was pure syn isomer. The pooled fractions from this 37 minute peak gave 500 mg of nearly pure syn isomer.

Final purification of syn-Re-(D,L)-N,N'-1,2-ethylenediylbiscysteine, diethyl ester was accomplished by HPLC using the conditions described above. 500 mg of the sample was dissolved in 4.0 mL of acetonitrile and purified in 1 mL portions to give 210 mg of violet solid. A sample of 460 mg of this violet solid was recrystallized from a minimal amount of hot ethanol (5 mL) to give 302 mg of violet crystals (MP 164°–170° C.), which were used for characterization.

Elemental Analysis:

| Element | Calculated | Found |
|---------|------------|-------|
| % C | 27.52 | 27.53 |
| % H | 4.04 | 3.91 |
| % N | 5.35 | 5.31 |
| % S | 12.25 | 12.32 |

Crystal Structure of syn-Re-(D,L)-N,N'-1,2-ethylenediylbiscysteine, diethyl ester Purple, monoclinic plates (0.18×0.07×0.35 mm), were isolated from acetonitrile by slow evaporation. The X-ray data were collected on an Enraf-Nonius CAD4 diffractometer using Mo $K_\alpha$ radiation. The cell parameters were obtained by a least-squares fit of 25 reflections ($3.1° \leq 2\theta \leq 60.0°$). Crystal data and details of data collection are given in the Table I. The structure was solved by automated Patterson analysis (PHASE) and refined by full-matrix least squares methods. Scattering factors were taken from the *International Tables for X-ray Crystallography*, vol. IV, including anomalous terms for Re, and S. The final agreement factor (R) was 0.031, with the largest residual density of $1.56e/Å^3$ near Re.

Crystallographic Data for syn-Re-(D,L)-N,N'-1,2-ethylenediylbiscysteine, diethyl ester

| formula | $C_{12}H_{21}N_2O_5S_2Re$ |
|---|---|
| space group | $P2_1/n$ (No. 14) |
| a, Å | 12.411 (4) |
| b, Å | 11.040 (2) |
| c, Å | 13.247 (4) |
| β, deg | 100.27 (1) |
| Z | 4 |
| fw | 523.67 |
| T, °C | −70 |
| V, $Å^3$ | 1786.0 |
| μ (Mo, $K_\alpha$), $cm^{-1}$ | 71.41 |
| Dc, g/cc | 1.947 |
| R | 0.031 |
| $R_w$ | 0.028 |

Examples 2 and 3

Synthesis of syn-Tc-99m-(D,L)-N,N'-1,2-ethylenediylbiscysteine, diethyl ester, and anti-Tc-99m-(D,L)-N,N'-1,2-ethylenediylbiscysteine, diethyl ester (D,L)-N,N'-1,2-ethylenediylbiscysteine, diethyl ester oxalate (3 mg) was dissolved in 0.05M phosphate buffer, pH 8 (1.0 mL), and treated with 50–150 mCi of Tc-99m $TcO_4^-$ from a DuPont Mo-99/Tc-99m generator, and 5–10 μL of a 5 mg/mL solution of $SnCl_2 \cdot 2H_2O$ in absolute ethanol. After 15 minutes at room temperature, the reaction was analyzed by TLC (R. C. Walovitch et al., *J. Nucl. Med.* 1989, 30, 1892–1901). The isomeric syn and anti complexes were separated by HPLC on a Zorbax® RX-C8 4.6 mm×25 cm column using a 35% acetonitrile/water mobile phase and a flow rate of 1.5 mL/min. The isomeric purity of each product fraction was >90%. The volatiles were evaporated from each fraction and the residue was dissolved in 0.9 wt % saline (typically 15 mCi/mL).

Example 4

Synthesis of Tc-99m-(L,L)-N,N'-1,2-ethylenediylbiscysteine, diethyl ester (L,L)-N,N'-1,2-ethylenediylbiscysteine, diethyl ester, dihydrochloride (3 mg) was dissolved in 0.05M phosphate buffer, pH 8 (1.0 mL), and treated with 50–150 mCi of Tc-99m $TcO_4^-$ from a DuPont Mo-99/Tc-99m generator, and 5–10 μL of a 5 mg/mL solution of $SnCl_2 \cdot 2H_2O$ in absolute ethanol. After 15 minutes at room temperature, the reaction was analyzed by TLC (R. C. Walovitch et al., *J. Nucl. Med.* 1989, 30, 1892–1901). The product was purified by HPLC on a Zorbax® RX-C8 4.6 mm×25 cm column using a 35% acetonitrile/water mobile phase and a flow rate of 1.5 mL/min. The purity of the product fraction was >90%. The volatiles were evaporated from the product fraction and the residue was dissolved in 0.9 wt % saline (typically 15 mCi/mL).

Example 5

Synthesis of Tc-99m-(D,D)-N,N'-1,2-ethylenediylbiscysteine, diethyl ester

The preparation of the compound of Example 5 followed the procedure outlined in Example 4, but started with (D,D)-N,N'-1,2-ethylenediylbiscysteine, diethyl ester, dihydrochloride.

Example 6

Biodistribution in Rhesus monkeys

Three adult male Rhesus monkeys were used for planar scintigraphic imaging. Anesthesia was induced with ketamine and maintained with 1–2% halothane in a 70/30 mixture of nitrous oxide and oxygen. Images were acquired using an attenuation-corrected conjugate view method (Eary, JF, Appelbaum, FL, Durack, L, and Brown, P, *Preliminary validation of the opposing view method for quantitative gamma camera imaging*, Med. Phys., V. 16, No. 3, pp382–387, 1989).

All acquisitions were performed using a Picker Digital Dyna Camera and a Siemens MicroDELTA terminal/MAXDELTA system. A high resolution parallel-hole collimator ("HEX48") was mounted on the camera. The general static acquisition protocol was employed, using an acquisition matrix of 128 by 128 pixels, in word mode. Linearity, Z- and uniformity correction as provided for in the camera console, were employed and maintained.

To provide correction for attenuation, a transmission image of each animal was required. This had to be acquired in such a fashion as to permit the location of individual organs to be delineated from an aligned emission image. To do this, an 18-inch commercial refillable flood source (Nuclear Associates, Carle Place, N.Y.) was filled with water on a flat, horizontal surface. It was then loaded with between 20 mCi (740 Mbq) and 30 mCi (1110 Mbq) of $Tc99mO_4^-$, and placed on a rolling cart. A Picker high-resolution collimator was then placed atop the source and the cart positioned under the patient examination table of the camera.

For each animal, a transmission image was acquired immediately prior to the control study injection, in the following fashion: An initial "flood" image was taken of the collimated source with neither the animal nor the examination table in place. Without moving anything else, the examination table, with the anesthetized animal, was placed between the source and the camera. Images were then taken of both the upper and lower portions of the body using a 128×128 pixel matrix in word mode. Table positioning was restricted by the track system so that positioning markers were necessary only for the dimension parallel to the animal's vertical axis.

Without moving the camera, the source was withdrawn and removed from the room. Adjustments to the camera-subject distance were made only by raising or lowering the table. The control compound was then injected and the control study begun. In this way, organs could be identified from the control study and the regions applied to the transmission study to determine attenuation correction factors on a per-organ basis. In addition, an "efficiency" factor was determined from images taken of a small flask containing a measured amount of radioactivity.

Following the injection of Tc-99m labeled materials, images were acquired of each animal using "spot" views over the upper and lower portions of the body with conjugate views (i.e. 180-degree opposed views) for each.

The resulting image data was analyzed by creating regions of interest (ROI's) for each organ and determining the sum of the recorded gamma photons for each organ in each view. From the transmission view, an attenuation correction factor was derived for each organ and the activity in the organ determined by taking the square root of the product of the ROI sums for conjugate views of the organ and then multiplying by the attenuation correction factor for that organ and then by the efficiency factor.

Each animal was imaged with Tc-99m-(L,L)-N,N'-1,2-ethylenediylbiscysteine, diethyl ester in order to serve as its own control. One test isomer was then administered to each of the monkeys. Frequent blood samples were drawn from a peripheral leg vein. Regions of interest were drawn around all pertinent organs and time-activity curves were constructed. The accumulated radioactivity in various organs is recorded in the tables below.

TABLE I

BIODISTRIBUTION IN RHESUS MONKEYS AFTER 30 MINUTES
(Numbers expressed as a percentage of the initial injected dose)

| Example # | Brain | Gall Bladder | Urinary Bladder |
|---|---|---|---|
| 2 | 3.4 | 2.2 | 58 |
| 3 | 2.1 | 2.7 | 4.2 |
| 4 | 5.8 | 10 | 29 |
| 5 | 1.7 | 5.5 | 5.0 |

TABLE II

BIODISTRIBUTION IN RHESUS MONKEYS AFTER 60 MINUTES
(Numbers expressed as a percentage of the initial injected dose)

| Example # | Brain | Gall Bladder | Urinary Bladder |
|---|---|---|---|
| 2 | 3.0 | 6.2 | 74 |
| 3 | 1.8 | 6.4 | 4.0 |
| 4 | 5.6 | 17 | 42 |
| 5 | 1.4 | 5.2 | 15 |

UTILITY

The biodistribution results shown in Tables I and II demonstrate that rapid renal excretion is highly dependent on the stereochemistry of the Tc-99m complex. syn-Tc-99m-(D,L)-N,N'-1,2-ethylenediylbiscysteine, diethyl ester (Example 2) is the most rapidly excreted with 58% and 74% in the urinary bladder after 30 and 60 minutes, respectively. Also noteworthy is the low uptake in other organs, especially the gall bladder, which is indicative of the level of liver uptake. Low background and rapid, efficient excretion are important features in renal imaging agents, allowing high quality images to be obtained with the minimal amount of radiopharmaceutical administered to the patient.

From the above results it is shown that complexes of the present invention show low liver activity, and rapid renal excretion. Further, the ease of preparation and stability of the Tc-99m complexes makes these complexes superior renal imaging agents.

What is claimed is:

1. The compound:

(D,L)-N,N'-1,2-ethylenediylbiscysteine, diethyl ester and pharmaceutically suitable salts thereof.

2. The compound:

syn-Tc-99m-(D,L)-N,N'-1,2-ethylenediylbiscysteine, diethyl ester and pharmaceutically suitable salts thereof.

3. A kit comprising a predetermined quantity of a sterile, non-pyrogenic reducing agent for reducing a preselected radionuclide, and a preselected quantity of the compound of claim 1.

4. A kit of claim 3 wherein the reducing agent is a stannous salt for reducing technetium-99m.

* * * * *